US008118845B2

(12) United States Patent
White (10) Patent No.: US 8,118,845 B2
(45) Date of Patent: Feb. 21, 2012

(54) APPARATUS AND PROCEDURE FOR ANTERIOR CERVICAL MICRODISKECTOMY

(76) Inventor: William M White, Phoenix, AZ (US)

( * ) Notice: Subject to any disclaimer, the term of this patent is extended or adjusted under 35 U.S.C. 154(b) by 1010 days.

(21) Appl. No.: 12/012,367

(22) Filed: Feb. 1, 2008

(65) Prior Publication Data

US 2009/0198239 A1     Aug. 6, 2009

(51) Int. Cl.
*A61B 17/00* (2006.01)
*A61B 17/68* (2006.01)
(52) U.S. Cl. ............ 606/279; 606/79; 606/80; 606/86 R
(58) Field of Classification Search .......... 606/79–86 R, 606/279; 623/17.11–17.16
See application file for complete search history.

(56) References Cited

U.S. PATENT DOCUMENTS

| | | | | |
|---|---|---|---|---|
| 4,059,115 | A * | 11/1977 | Jumashev et al. ............... | 606/82 |
| 5,306,307 | A * | 4/1994 | Senter et al. ............... | 623/17.16 |
| 5,499,984 | A * | 3/1996 | Steiner et al. ............... | 606/80 |
| 5,741,261 | A * | 4/1998 | Moskovitz et al. ............ | 606/79 |
| 6,443,967 | B1 | 9/2002 | Kadavy et al. ............... | 606/159 |
| 6,592,625 | B2 * | 7/2003 | Cauthen ..................... | 623/17.16 |
| 6,805,697 | B1 * | 10/2004 | Helm et al. ..................... | 606/92 |
| 6,805,715 | B2 * | 10/2004 | Reuter et al. ............... | 623/17.12 |
| 7,014,633 | B2 * | 3/2006 | Cragg .......................... | 604/500 |
| 7,128,746 | B2 * | 10/2006 | Singer et al. ..................... | 606/90 |
| 7,179,255 | B2 * | 2/2007 | Lettice et al. ..................... | 606/32 |
| 7,585,300 | B2 * | 9/2009 | Cha .................................. | 606/80 |
| 7,963,915 | B2 * | 6/2011 | Bleich .......................... | 600/184 |
| 2002/0029056 | A1 * | 3/2002 | Hall et al. ..................... | 606/170 |
| 2002/0138091 | A1 * | 9/2002 | Pflueger ........................ | 606/170 |
| 2004/0244806 | A1 * | 12/2004 | Ferree .......................... | 128/898 |
| 2005/0049604 | A1 * | 3/2005 | Singer et al. ..................... | 606/90 |
| 2005/0197661 | A1 * | 9/2005 | Carrison et al. ............... | 606/79 |
| 2005/0203527 | A1 * | 9/2005 | Carrison et al. ............... | 606/80 |
| 2006/0004369 | A1 * | 1/2006 | Patel et al. ..................... | 606/79 |
| 2006/0229624 | A1 * | 10/2006 | May et al. ..................... | 606/79 |
| 2006/0264957 | A1 * | 11/2006 | Cragg et al. ..................... | 606/80 |
| 2007/0162136 | A1 * | 7/2007 | O'Neil et al. ............... | 623/17.12 |
| 2007/0168043 | A1 * | 7/2007 | Ferree .......................... | 623/17.16 |
| 2007/0213735 | A1 * | 9/2007 | Saadat et al. ..................... | 606/79 |
| 2007/0260254 | A1 * | 11/2007 | Lesinski ........................ | 606/80 |
| 2008/0269754 | A1 * | 10/2008 | Lutz et al. ..................... | 606/79 |
| 2009/0177202 | A1 * | 7/2009 | May et al. ..................... | 606/79 |

* cited by examiner

*Primary Examiner* — Thomas C. Barrett
*Assistant Examiner* — Matthew Lawson
(74) *Attorney, Agent, or Firm* — Tod R. Nissle, P.C.

(57) ABSTRACT

A method is provided to perform an anterior cervical microdiskectomy to remove at least one bone spur on a pair of adjacent vertebrae in a spinal column that includes a posterior longitudinal ligament. Each vertebra contacts a disk positioned therebetween. The disk includes an annulus and a nucleus. The method comprises the steps of removing a portion of the annulus of the disk; removing the nucleus of the disk; removing the vertebral plates with a first burr; removing a portion of the bone spur with a second burr having a spherically shaped abrading head; and, providing a third burr. The third burr comprises an elongate shaft having a distal end and a proximate end; and, a head attached to and extending outwardly from the distal end of the shaft. The head includes a smooth end surface; and, a smooth rounded peripheral edge circumscribing the end surface. The end surface and rounded peripheral edge are shaped and dimensioned to contact rotatably the posterior longitudinal ligament without cutting or puncturing the ligament. The head also includes an abrading surface extending away from the smooth end surface and from the smooth rounded peripheral edge and inwardly toward the shaft. The method also includes the steps of rotating the third burr; contacting the posterior longitudinal ligament with at least a portion of the smooth end surface and the smooth rounded peripheral edge, and, contacting the bone spur with the abrading surface.

1 Claim, 10 Drawing Sheets

APPARATUS AND PROCEDURE FOR ANTERIOR CERVICAL MICRODISKECTOMY

More particularly, this invention pertains to an apparatus and method for performing an anterior cervical microdiskectomy.

An intervertebral disc is a soft tissue compartment connecting the vertebra bones in a spinal column. Each healthy disc consists of two parts, an outer annulus fibrosis (hereinafter "the annulus") and an inner nucleus pulposes (hereinafter "the nucleus"). The annulus completely circumscribes and encloses the nucleus. The annulus is connected to its adjacent associated pair of vertebrae by collagen fibers.

The intervertebral disc is an example of a soft tissue compartment adjoining first and second bones (vertebra) having an initial height and an initial width. Other joints consisting of a soft tissue compartment adjoining at least first and second bones having an initial height and an initial width include the joints of the hand, wrist, elbow, shoulder, foot, ankle, knee, hip, etc.

In one scenario, when a disc is damaged, the annulus ruptures and the nucleus herniates. Diskectomy surgery can, if desired, be utilized to remove the extruded nucleus, leaving behind the ruptured annulus. The ruptured annulus is, by itself, less effective in controlling motion and supporting the loads applied by the adjacent pair of vertebrae. With time, the disc flattens, widens, and bulges, compressing nerves and producing pain. Excessive loads are transmitted to each vertebra. Each vertebra tends to develop bone spurs to compensate for higher loads. In addition, when a disk or joint is inflamed from arthritis or injury, the body tries to heal by calcification and this results in a bone spur which grows on the vertebra. The bone spurs further compress nerves and/or the spinal chord, producing pain, and even more importantly, paralysis. In another scenario, even if the extruded nucleus is not removed, bone spurs form on a vertebra. In still another scenario, bone spurs form on a vertebra even if the nucleus is not extruded.

During an anterior cervical microdiskectomy, a disc adjacent the vertebra is removed, a bone spur(s) is removed from a vertebra, a bone graft implant is inserted in the area vacated when the disc is removed, and a plate or other fixation means is attached to the vertebra and at least one adjacent vertebra to fix substantially the position of the construct. During the anterior cervical microdiskectomy, a rotating burr with a spherical head is utilized to remove the bone spur.

The above-described anterior cervical microdiskectomy procedure is well-accepted and there appears to be no pressure in the art to alter the procedure. In many cases, however, it is possible to improve an existing apparatus or procedure.

Accordingly, it would be highly desirable to provide an improved anterior cervical microdiskectomy procedure and apparatus.

Therefore, it is a principal object of the invention to provide an improved cervical microdiskectomy apparatus and methodology.

This and other, further and more specific objects and advantages of the invention will be apparent from the following detailed description of the invention, taken in conjunction with the drawings, in which:

Briefly, in accordance with the invention, I provide an improved burr to simultaneously during an anterior cervical microdiskectomy contact the posterior annulus and the posterior longitudinal ligament without cutting or puncturing the ligament, and abrade a vertebral bone spur that is located adjacent the posterior longitudinal ligament. The burr comprises an elongate shaft having a distal end and a proximate end; and, a head attached to and extending outwardly from the distal end of the shaft. The head includes a smooth end surface; a smooth rounded peripheral edge circumscribing the end surface, the end surface and rounded peripheral edge shaped and dimensioned to contact rotatably the posterior longitudinal ligament without cutting or puncturing the ligament; and, an abrading surface extending away from the smooth end surface and the smooth rounded peripheral edge and inwardly toward the shaft.

In accordance with another embodiment of the invention, I provide an improved method to perform an anterior cervical microdiskectomy to remove at least one bone spur on a pair of adjacent vertebrae in a spinal column that includes a posterior longitudinal ligament. Each vertebra contacts a disc positioned therebetween. The disc includes an annulus and a nucleus. The method comprises the steps of removing a portion of the annulus of the disc; removing the nucleus of the disc; removing a portion of the bone spur with a first burr having a spherically shaped abrading head; and, providing a second burr. The second burr comprises an elongate shaft having a distal end and a proximate end; and, a head attached to and extending outwardly from the distal end of the shaft. The head includes a smooth end surface; and, a smooth rounded peripheral edge circumscribing the end surface. The end surface and rounded peripheral edge are shaped and dimensioned to contact rotatably the posterior longitudinal ligament without cutting or puncturing the ligament. The head also includes an abrading surface extending away from the smooth end surface and from the smooth rounded peripheral edge and inwardly toward the shaft. The method also includes the steps of rotating the second burr; contacting the posterior longitudinal ligament with at least a portion of the smooth end surface and the smooth rounded peripheral edge, and, contacting the bone spur with the abrading surface.

Turning now to the drawings, which depict the presently preferred embodiments of the invention for the purpose of illustrating the practice thereof and not by way of limitation of the scope of the invention, and in which like reference characters refer to corresponding elements throughout the several views, FIGS. 1 to 7 illustrate an anterior cervical microdiskectomy procedure performed in accordance with the invention.

Figure 1:
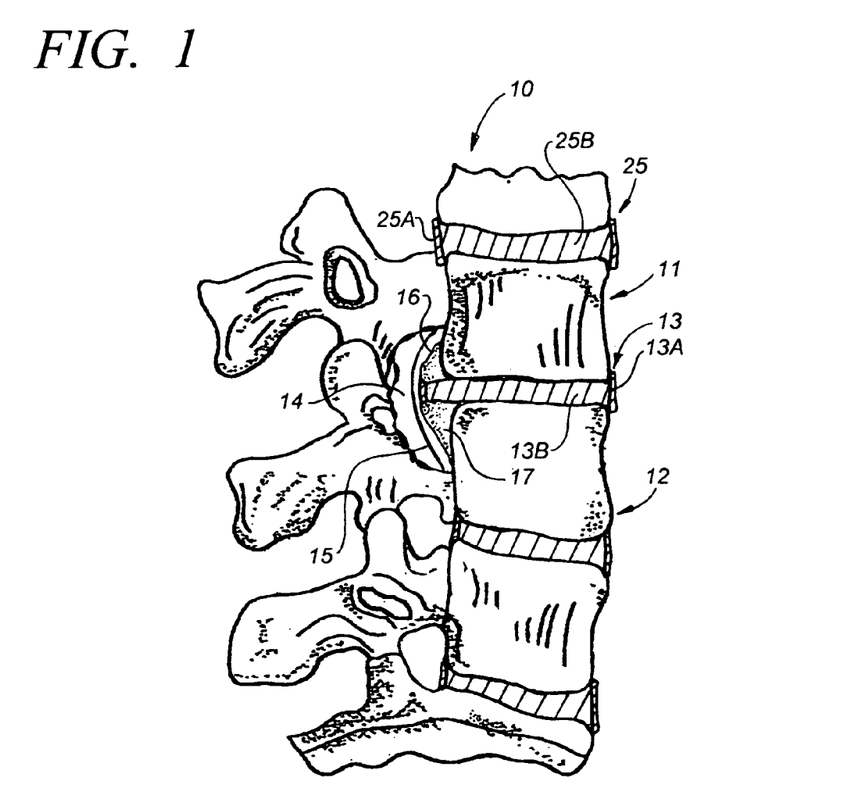
FIG. 1 is a side view of a portion of a spinal column illustrating an improved anterior cervical microdiskectomy procedure and apparatus in accordance with the principles of the invention.

In FIG. 1, a portion of a spinal column is generally indicated by reference character 10 and includes a pair of adjacent vertebra 11 and 12 with disk 13 interposed therebetween and contacting each vertebra 11 and 12. Disk 13 includes annulus 13A and nucleus 13B. Similarly, in FIG. 1, disk 25 includes annulus 25A and nucleus 25B.

Figure 13:
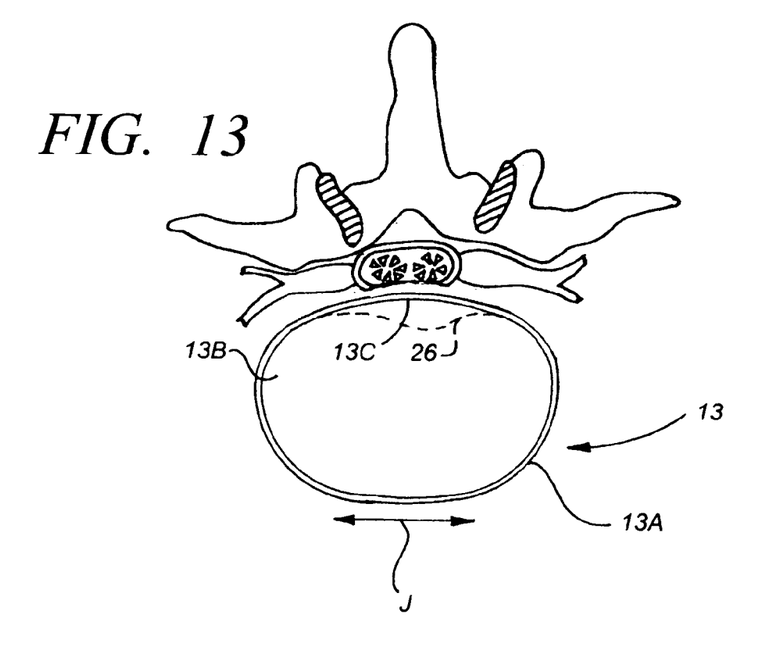
FIG. 13 is top view illustrating a bulging intervertebral disk of the type being treated by the process illustrated in FIGS. 1 to 7; and, FIG. 14 is a top view illustrating a normal healthy intervertebral disk.
Figure 14:
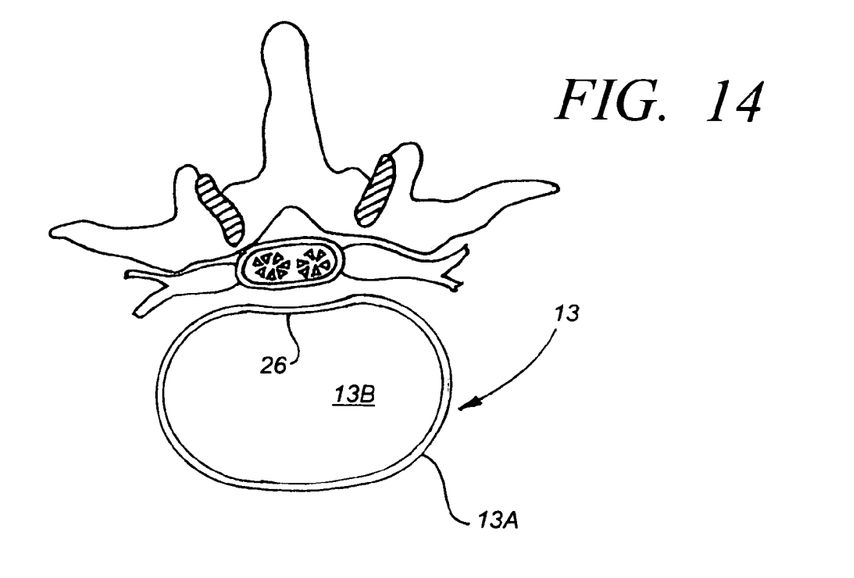

A disk 13 may, or may not, have a herniated nucleus, be flattened from its normal healthy configuration, etc. The disk 13 illustrated in FIG. 1 and treated using the process subsequently explained below with reference to FIGS. 2 to 7, is a bulging disk of the type illustrated in FIG. 13 wherein the bulge 13C protrudes outwardly from vertebra 11 and 12 toward the spinal chord. Vertebra 11 includes posterior osteophyte 16. Vertebra 12 includes posterior osteophyte 17. The posterior longitudinal ligament 15 extends along the spinal canal 14 and over osteophytes 16 and 17. Portions of osteophytes 16 and 17 extend behind the vertebral bodies 11 and 12. FIG. 1 illustrates the spinal column prior to carrying out an anterior cervical microdiskectomy.

The first step in the anterior cervical microdiskectomy procedure is to expose the anterior cervical spine and make a rectangular incision in the anteior annulus. A one to two centimeter length or piece, indicated by arrows J in FIG. 13, of the anterior disk annulus is excised. The remainder of the disk annulus is left intact along with the portion of the posterior longitudinal ligament that runs adjacent the vertebrae. The posterior portion of the annulus 13A that is left intact, along with the posterior longitudinal ligament 15, functions to protect the Dura and spinal cord during drilling with the various burrs.

The second step in the microdiskectomy is to enter and remove the nucleus of disk 13 with curettes or pituitary rongeur.

Figure 2:
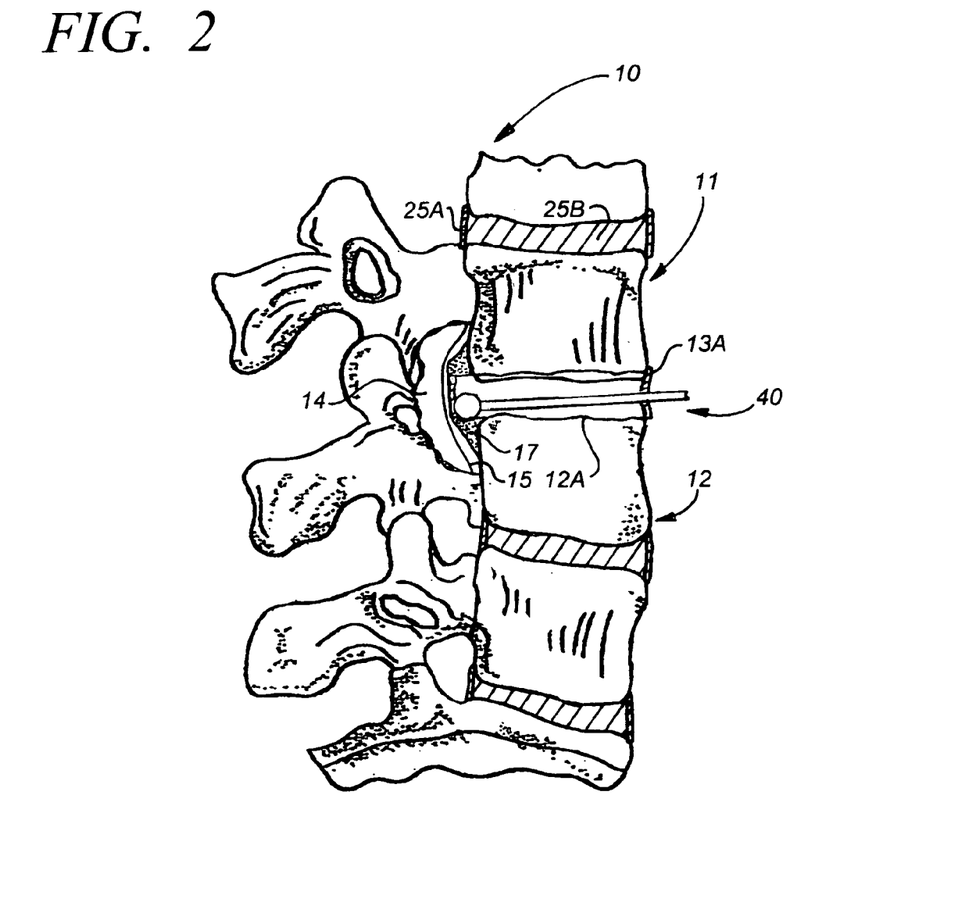
FIG. 2 is a side view of a portion of a spinal column further illustrating the improved anterior cervical microdiskectomy procedure and apparatus of the invention.

The third step in the microdiskectomy is to utilize a cutting burr to remove the opposing end plates of vertebrae 11 and 12 and produce surfaces 11A (in vertebra 11) and 12A (in vertebra 12). Removing the end plates allows bone material that is subsequently inserted intermediate vertebrae 11 and 12 to fuse more readily to the vertebrae 11, 12. The cutting burr typically has a spherical head with a diameter of about five mm. FIG. 2 illustrates the spinal column after the one to centimeter piece of the anterior annulus of disk 13 has been removed, after the nucleus of disk 13 has been removed, and after the adjacent end plates of vertebra 11 and 12 have been removed to produce surfaces 11A and 12A. If necessary, removal of the end plates, of a portion(s) of the annulus, and of the nucleus can also function to create a channel, or opening, that is large enough to enable the rotatable diamond burr 40 (and subsequently burr 50 or 60) to be inserted through the channel in the manner illustrated in FIG. 2 to remove portions of osteophytes 16 and 17. Diamond burr 40 typically has a diameter of about six millimeters (mm). It is possible that the height of the annulus is sufficient to permit access by burr 40, and that the end plates of vertebrae 11 and 12 need not be removed to form a tunnel or opening having a size sufficient to allow ingress and egress by burr 40. The end plates would still be removed to expose cancellous bone to improve the chance of bone growth into a graft that is interposed between vertebra 11 and 12.

The fourth step in the microdiskectomy is to utilize a diamond burr 40 to remove portions of osteophytes 16 and 17 in the manner illustrated in FIG. 2 while leaving the posterior annulus and posterior longitudinal ligament 15 in place to protect the spinal chord.

Figure 3:
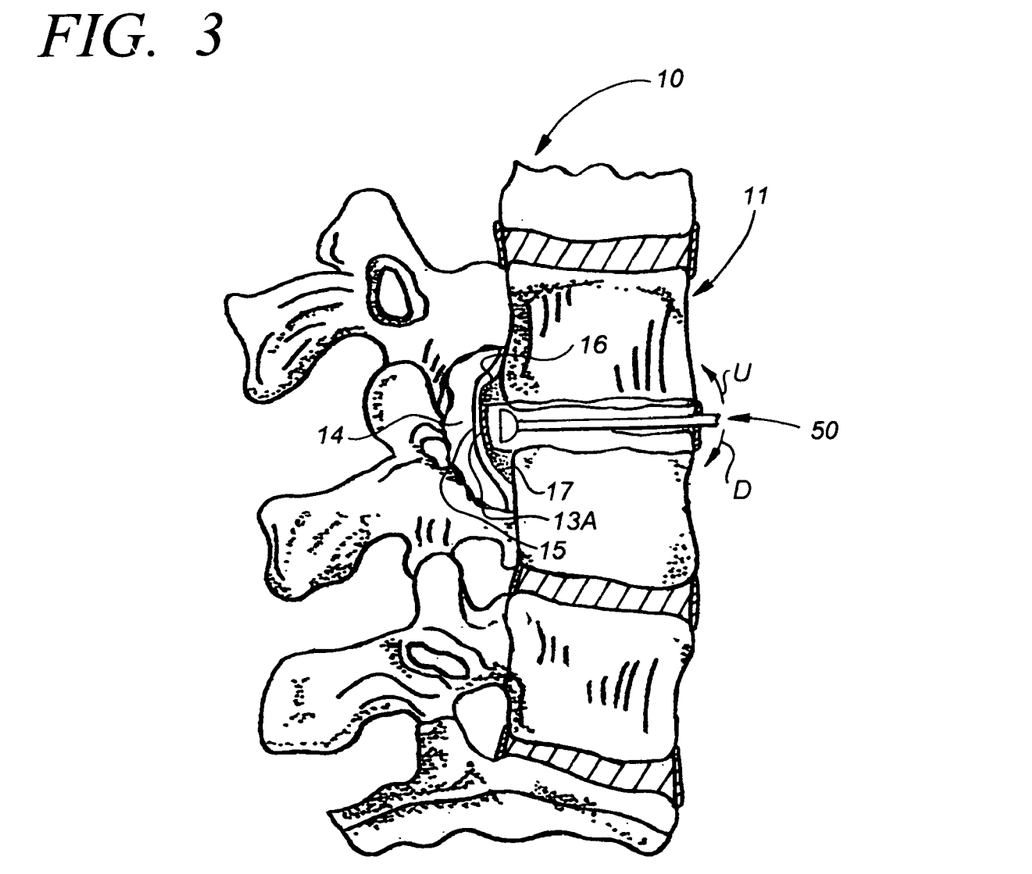
FIG. 3 is a side view of a portion of a spinal column further illustrating the improved anterior cervical microdiskectomy procedure and apparatus of the invention.

The fifth step in the microdiskectomy is to utilize burr 50 in the manner illustrated in FIG. 3 to remove substantially all of the remaining portions of osteophytes 16 and 17. In FIG. 3, the shaft 53 of burr 50 is substantially horizontal. The tunnel or opening formed in the manner described above by removing portions of the disk and vertebra enable shaft 53 to be tilted somewhat upwardly as indicated by arrow U or downwardly as indicated by arrow D from the horizontal to facilitate use of the head 51 of burr 50 to remove portions of osteophytes 16 and 17 that are illustrated in FIG. 3 and that extend upwardly behind vertebra 11 or downwardly behind vertebra 12, respectively. Sizing shaft 53 and the opening formed intermediate vertebrae 11 and 12 to permit the tilting of shaft 53 and head 51 is important in facilitating the removal of osteophytes 16 and 17.

Figure 4:
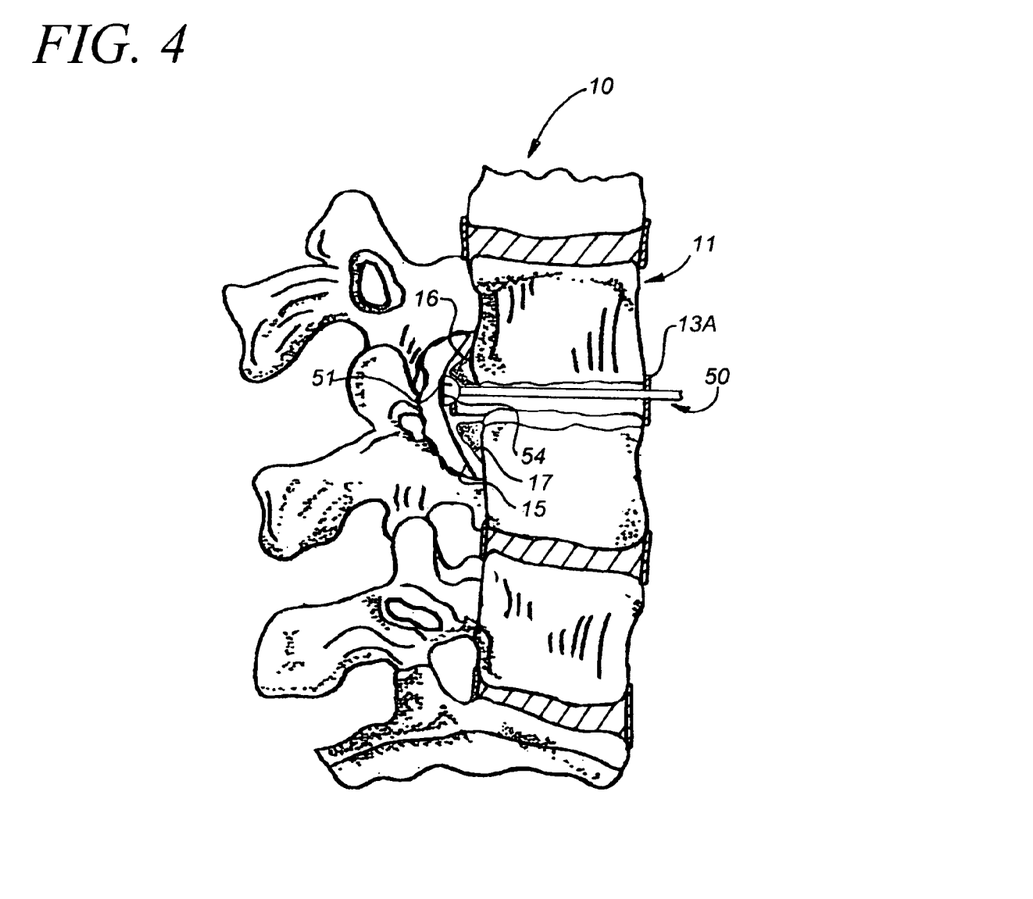
FIG. 4 is a side view of a portion of a spinal column further illustrating the improved anterior cervical microdiskectomy procedure and apparatus of the invention.
Figure 5:
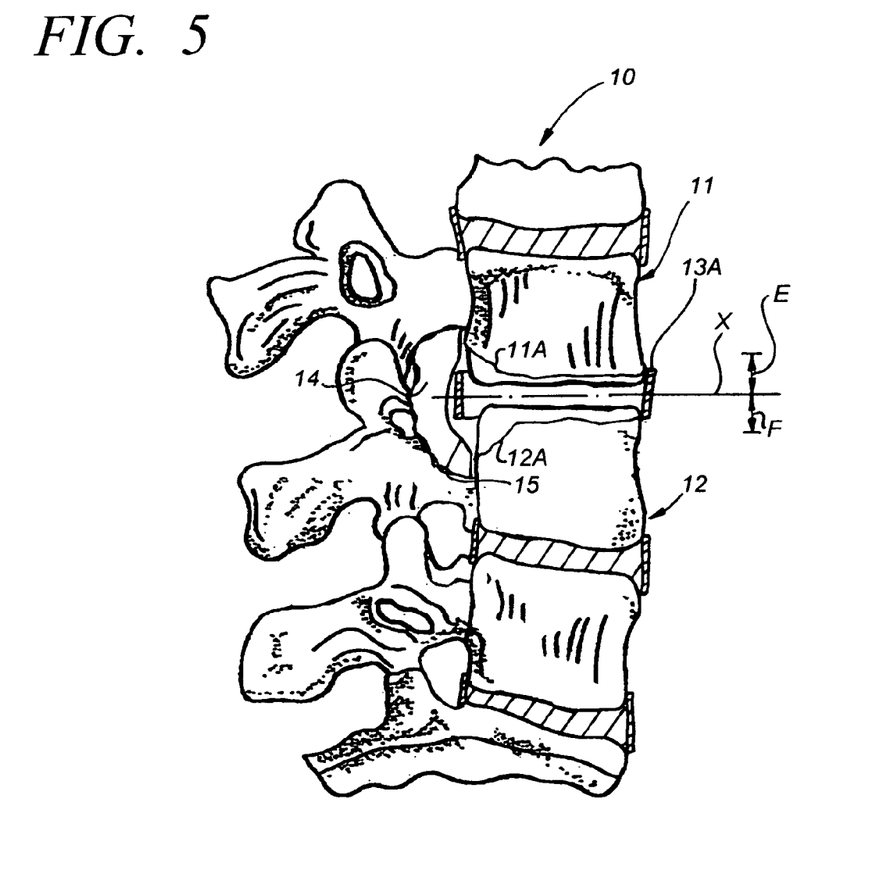
FIG. 5 is a side view of a portion of a spinal column further illustrating the improved anterior cervical microdiskectomy procedure and apparatus of the invention.

In FIG. 4, undermining burr 50 (FIG. 9) is rotated while at least a portion of end surface 54 and rounded peripheral edge 56 contact the annulus and the posterior longitudinal ligament and while at least a portion of abrading surface 52 undercuts osteophyte 16 to remove portions of osteophyte 16 that extend behind vertebra 11. This procedure can be accomplished if the posterior annulus is removed; however, as noted earlier, it is preferred that the posterior annulus remain in place when burr 50 is utilized. Consequently, when burr 50 is used to removed portions of osteophytes 16 and 17, the end surface 54 can contact the posterior annulus and will not contact the posterior longitudinal ligament. Undermining burr 50 is similarly utilized to remove portions of osteophyte 17 that extend behind vertebra 12. When undermining burr 50 removes portions of osteophytes 16 and 17, portions of vertebral bodies 11 and 12 are, as indicated by reference characters 11 and 12 in FIG. 5, also removed. FIG. 5 illustrates spinal column 10 after osteophytes 16 and 17 have been substantially removed using burr 40 and using undermining burr 50. In FIG. 5, the posterior annulus and other remaining portion(s) of the annulus have not yet been removed.

Flat end surface 54 and non-cutting rounded peripheral edge 56 permit contact with the posterior annulus and posterior longitudinal ligament with minimal displacement of the posterior longitudinal ligament inwardly toward the spinal canal 14 without piercing, penetrating, or injuring the posterior annulus or posterior longitudinal ligament and spinal chord. This facilitates removal of osteophytes 16 and 17. It is also important, however, to continue moving the head of burr 50 and to not let end surface 54 of head 51 contact and rotate on a portion of the posterior longitudinal ligament for any extended period of time. Allowing end surface 54 to set and rotate against a specific portion of the posterior annulus or posterior longitudinal ligament allows the rotating end surface 54 to generate frictional heat which can injure and burn the posterior annulus or ligament. Continuously moving head 51 and end surface 54 back and forth over the posterior annulus or ligament, along with continuous irrigation with saline, avoids burning the posterior annulus or posterior longitudinal ligament. When burr 50 is utilized to remove osteophytes 16 and 17, care is taken to utilize the burr 50 only in the central area of vertebra 11 and 12, and to not move burr 50 to locations that are too far away from plane X. This central area extends upwardly (a distance indicated by arrows E) and downwardly (a distance indicated by arrows F) from plane X. As is illustrated in FIG. 5, plane X is generally normal to the plane of the page of paper of the drawings, extends through the annulus of disk 13, and is centered between vertebra 11 and 12. The distance indicated by arrows E is in the range of six to ten mm, as is the distance indicated by arrows F. Use of burr 50 is limited to this central area because it is important to avoid contacting laterally a vertebral artery that is directly anterior to the nerve root. Extreme caution should be used if attempts are made to use a burr 50 for lateral decompression and/or the foraminotomy.

Figure 6:
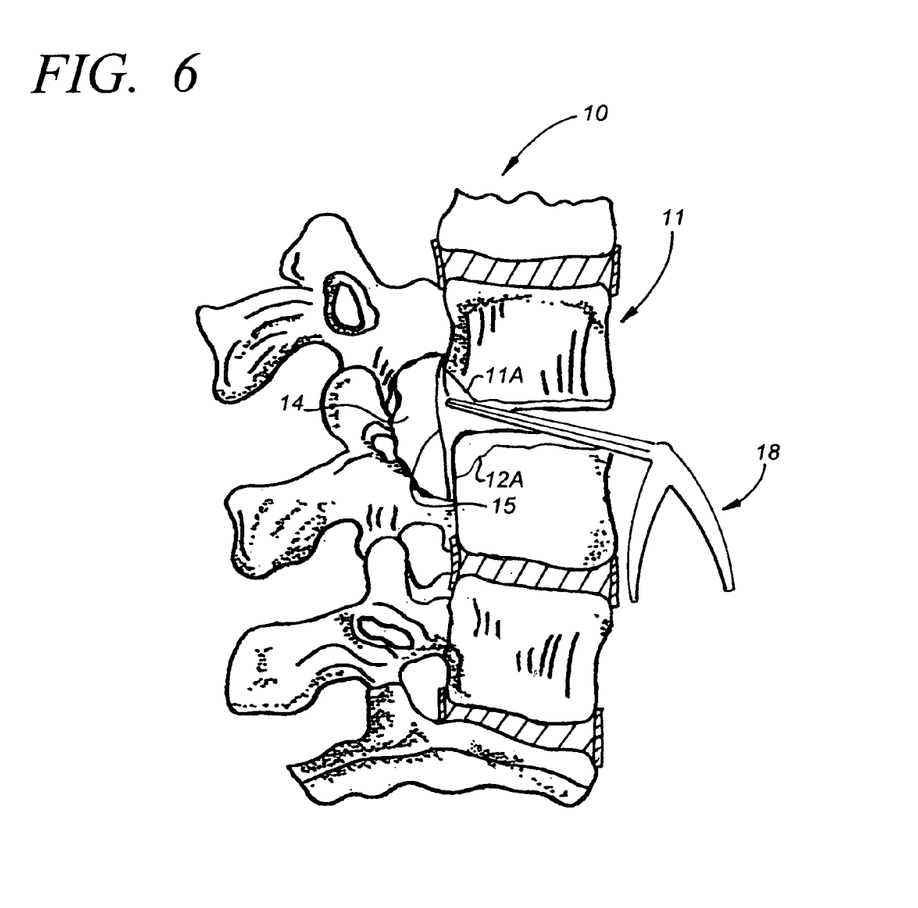
FIG. 6 is a side view of a portion of a spinal column further illustrating the improved anterior cervical microdiskectomy procedure and apparatus of the invention.

The sixth step in the microdiskectomy is to remove both the remaining portions of the annulus 13A (including the posterior annulus), along with the portion of the posterior longitudinal ligament that is adjacent the opening in the vertebral bodies 11 and 12 that is formed by removal of osteophytes 16 and 17. Curettes and small Kerrison surgical instruments are utilized to remove the remaining portion of the annulus and to remove a portion of the posterior longitudinal ligament. In FIG. 6, the remainder of the annulus 13A has been removed, and Kerrison instrument 18 is about to be utilized to remove a portion of the posterior longitudinal ligament 15.

After the remaining portions of the annulus is removed and the desired portion of the posterior longitudinal ligament is removed, the seventh step in the microdiskectomy is to confirm decompression by palpating with a dental tool. The nerve root foramina may be checked with a nerve hook. As is illustrated in FIG. 7, epidural bleeding is controlled with Gelfoam (TM) 19 soaked in thrombin.

The eighth step in the microdiskectomy is to measure the interspace defect intermediate vertebral bodies 11 and 12 and to select and insert an implant 20, typically an allograft. A wedge shape is recommended with the smaller end directed toward the spinal canal and the larger end superficial. A wedge shape placed in this manner decreases the potential for migration of the implant 20 into the spinal canal and spinal cord.

Figure 7:
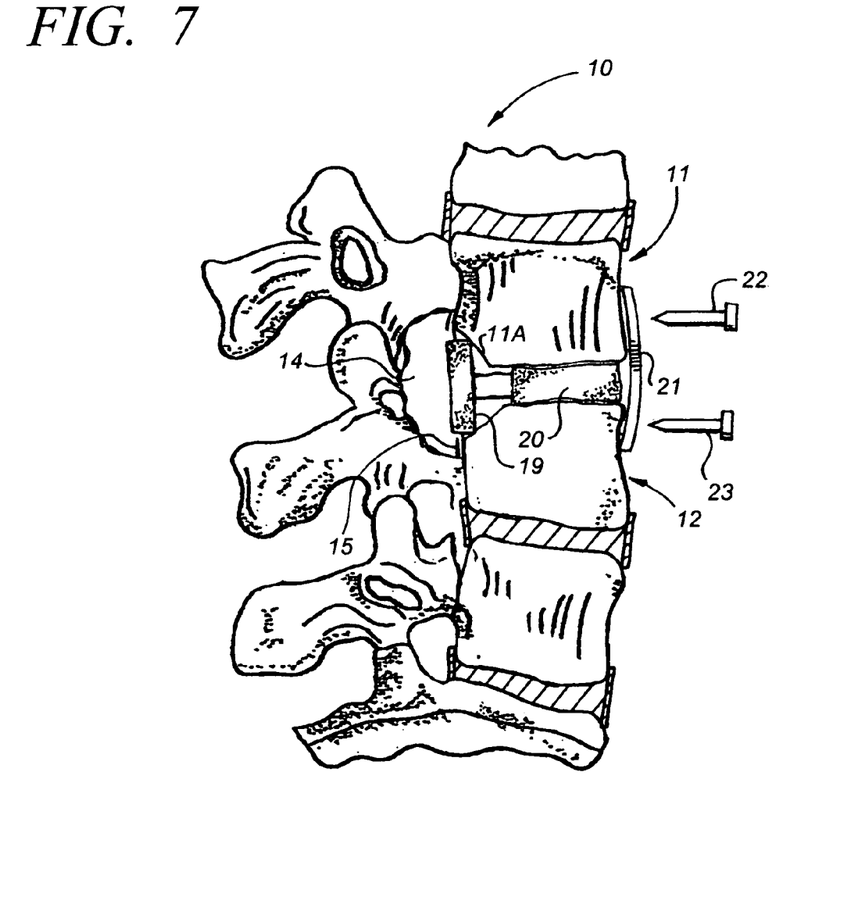
FIG. 7 is a side view of a portion of a spinal column further illustrating the improved anterior cervical microdiskectomy procedure and apparatus of the invention.

The ninth step in the microdiskectomy is to secure a plate 21 with screws 22 and 23 or other fastening means in the position illustrated in FIG. 7. Plate 21 limits the potential for extrusion of the graft, and immobilizes the vertebral bodies 11 and 12 to increase the potential for fusion.

Figure 8:
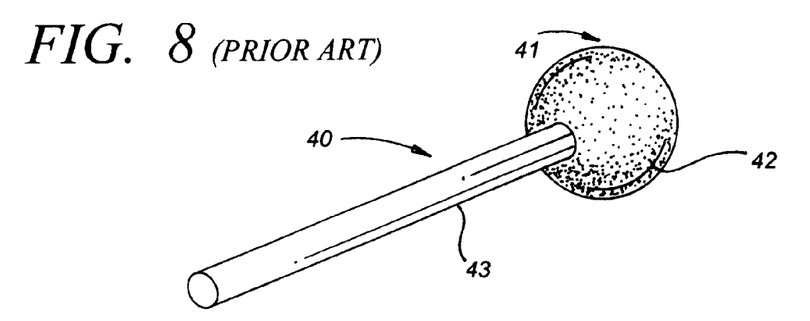
FIG. 8 is a perspective view illustrating a burr having a spherical abrasive head.

In FIG. 8, rotatable diamond burr 40 includes shaft or shaft 43 and spherical head 41 with abrading spherically shaped surface 42. Shaft 43 ordinarily is placed in a drill or other instrument that rotates shaft 43 and head 41 about the longitudinal axis of shaft 43.

Figure 9:
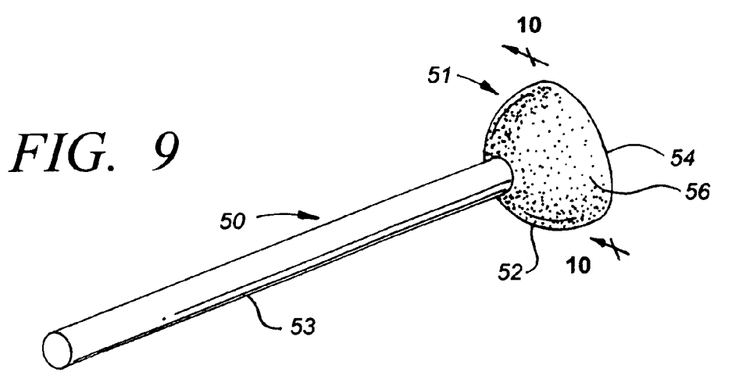
FIG. 9 is a perspective view illustrating a burr constructed in accordance with the invention.

In FIG. 9, rotatable undermining burr 50 includes shaft 53 and hemispherical head 51 with abrading hemispherically shaped surface 52. Head 51 also includes smooth non-abrading non-cutting, non-piercing, non-tearing bottom surface 54 and rounded peripheral edge 56. Surface 52 extends away from edge 56 and surface 54 toward shaft 53. Smooth surface 54 can be flat, convex (as indicated by dashed line 54A), concave, or can undulate. Regardless, however, of the shape of surface 54, surface 54 is smooth and can contact and rotate over the posterior annulus or posteriorlongitudinal ligament without abrading, cutting, piercing and/or tearing the annulus or ligament. For example, if surface 54 were shaped like a cone, this would not be appropriate because a cone comes to a point. Such a point could easily pierce the annulus or longitudinal posterior ligament. Consequently, a relatively smooth, continuous, substantially flat surface 54, 54A is critical and is preferred in the practice of the invention. Similarly, the shape and dimension of the peripheral edge 56 of undermining burr 50 is critical in the practice of the invention. Edge 56 has a height indicated by arrows X in FIG. 10 and functions as the bridge between smooth surface 54 and abrasive surface 52. Edge 56 can not be sharp, can not comprise a cutting edge, and can not abrade. In one embodiment of the invention, the outer surface of edge 56 is curved and smooth. The curvature may simulate a portion of a circle or an ellipse or other arcuate shape. If the curvature simulates a circle, the radius R of edge 56 (FIG. 12) should be large enough to prevent edge 56 from functioning as an edge that cuts the annulus or posterior longitudinal ligament when burr 50 is utilized to remove osteophytes. By way of example, and not limitation, the radius R is typically at least one thirty-second of an inch, preferably at least one-sixteenth of an inch, and most preferably at least three thirty-seconds of an inch. If the radius of curvature fo edge 56 is too small, then edge 56 can, even if it is curved and smooth, function as a cutting edge, which is not acceptable in the practice of the invention. The abrading surface 52 of head 51 extends outwardly away from smooth edge 56 and inwardly toward the shaft 53. The smooth flat surface 54-smooth edge 56-outwardly and inwardly extending abrading surface 52 combination is critical in the practice of the invention. In another embodiment of the invention, the edge 56 has a small or non-existent radius and is functional as long as the edge does not cut or pierce the posterior longitudinal ligament on contact.

Figures 10, 11, 12:
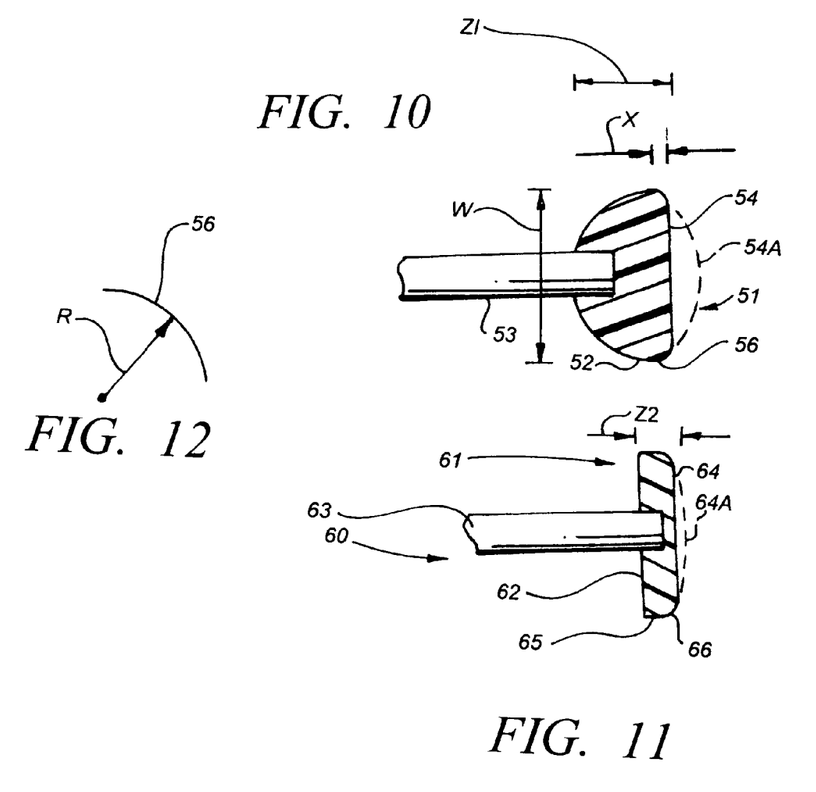
FIG. 10 is a section view of the portion of the burr of FIG. 9 further illustrating construction details thereof.
FIG. 11 is a section view of an alternate burr construction in accordance with the invention.
FIG. 12 is a diagram illustrating the necessary radius of curvature of a burr constructed in accordance with the invention.

FIG. 11 illustrates an alternate configuration of an undermining burr 60 that can be utilized in the practice of the invention. Burr 60 includes shaft 63, and generally cylindrically shaped head 61. Head 61 is provided with a smooth end surface 64 or 64A, and smooth, curved peripheral surface 66 that serves as a bridge between surface 64 and abrading surfaces 62 and 65.

The distal end of a shaft 53, 63 can be externally threaded and can turn into an internally threaded opening in head 51, 61, respectively, so that when the head 51, 61 is in the spinal column, shaft 53, 63 can be rotatably detached, and then reattached to head 51, 61, respectively. This permits, for example, a head 51, 61 to first be inserted between vertebra 11 and 12 to a desired location, permits the shaft 53, 63 to then be attached to the head 51, 61, and permits burr 50, 60 to then be rotated and used to remove an osteophyte. A shaft 53 can be detachably secured to a head 51 using a hook and bayonet configuration or any other desired configuration.

In one embodiment of the invention, it is desirable to minimize the height Z1, Z2 of the head 51, 61 of a burr 50, 60 (FIGS. 10 and 11). The height Z1, Z2 is preferably in the range of two to eight mm, preferably two to six mm, to facilitate ingress and egress of head 51, 61 between vertebra 11 and 12 and the posterior longitudinal ligament. Such a height Z1, Z2 can advantageously be utilized in conjunction with one or more of the other features of the invention set forth herein.

In another embodiment of the invention, it is desirable to utilize a burr head 51, 61 with a larger diameter or width W (FIG. 10) that is in the range of eight to sixteen millimeters. Such a width can advantageously be utilized in conjunction with one or more of the other features of the invention set forth herein. A diameter of less than eight mm is not preferred in the practice of the invention and tends to defeat one achievement of the invention, which is to facilitate removal of osteophytes intermediate the posterior longitudinal ligament and a vertebra 11, 12.

Having described the invention in such terms as to enable those of skill in the art to make and practice it, and having described the presently preferred Embodiments thereof, I claim:

Having described the invention in such terms as to enable those of skill in the art to make and practice it, and having described the presently preferred embodiments thereof, I claim:

1. A method to perform an anterior cervical microdiskectomy to remove at least one bone spur on a pair of adjacent vertebrae in a spinal column that includes a posterior longitudinal ligament, each vertebra contacting a disk positioned therebetween, the disk including an annulus and a nucleus, the method comprising the steps of
   (a) removing a portion of the annulus of the disk;
   (b) removing the nucleus of the disk;
   (c) removing a portion of the bone spur with a first burr having a spherically shaped abrading head;
   (d) providing a second burr comprising
     (i) an elongate shaft having a distal end and a proximate end; and,
     (ii) a head attached to and extending outwardly from said distal end of said shaft and including a smooth end surface,
       a smooth rounded peripheral edge circumscribing said end surface, said end surface and rounded peripheral edge shaped and dimensioned to contact rotatably the posterior longitudinal ligament without cutting or puncturing the ligament, and an abrading surface extending away from said smooth end surface and said smooth rounded peripheral edge and inwardly toward said shaft;
   (e) rotating said second burr; while simultaneously contacting the posterior annulus and the posterior longitudinal ligament, at least a portion of said smooth end surface and said smooth rounded peripheral edge contacting the posterior longitudinal ligament, and,
   (f) contacting the bone spur with said abrading surface.

* * * * *